US 6,734,304 B2

(12) United States Patent
Weintritt et al.

(10) Patent No.: US 6,734,304 B2
(45) Date of Patent: May 11, 2004

(54) METHOD FOR PRODUCING ASYMMETRICAL 4,6-BIS(ARYLOXY) PYRIMIDINE DERIVATIVES

(75) Inventors: Holger Weintritt, Langenfeld (DE); Uwe Stelzer, Burscheid (DE); Herbert Gayer, Monheim (DE); Walter Hübsch, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/221,889

(22) PCT Filed: Mar. 12, 2001

(86) PCT No.: PCT/EP01/02731

§ 371 (c)(1),
(2), (4) Date: Sep. 17, 2002

(87) PCT Pub. No.: WO01/72719

PCT Pub. Date: Oct. 4, 2001

(65) Prior Publication Data

US 2003/0092723 A1 May 15, 2003

(30) Foreign Application Priority Data

Mar. 24, 2000 (DE) .......................................... 100 14 607

(51) Int. Cl.[7] .............................................. C07D 239/52
(52) U.S. Cl. ............................ 544/319; 544/2; 544/65; 544/66
(58) Field of Search ............................ 544/319, 2, 65, 544/66

(56) References Cited

U.S. PATENT DOCUMENTS

| 5,677,453 | A | 10/1997 | Cramm et al. ............... 544/334 |
| 5,707,995 | A | 1/1998 | Munro et al. ................ 514/256 |
| 5,723,471 | A | 3/1998 | De Fraine ................... 514/274 |
| 5,849,910 | A | 12/1998 | Kameswaram ............... 544/319 |
| 5,883,250 | A | 3/1999 | Krüger et al. ............... 540/544 |
| 5,977,363 | A | 11/1999 | Wood et al. ................. 544/319 |
| 6,031,107 | A | 2/2000 | Heinemann et al. ......... 548/129 |
| 6,103,717 | A | 8/2000 | Heinemann et al. ..... 514/229.2 |
| 6,194,418 | B1 | 2/2001 | Seitz et al. ................. 514/256 |
| 6,235,743 | B1 | 5/2001 | Gayer et al. ................ 514/269 |
| 6,251,899 | B1 | 6/2001 | Gerdes et al. ........... 514/229.2 |
| 6,306,855 | B1 | 10/2001 | Heinemann et al. ........ 514/241 |
| 6,337,401 | B1 | 1/2002 | Heinemann et al. ........ 548/187 |
| 6,359,133 | B2 | 3/2002 | Gayer et al. ................ 544/319 |
| 6,380,386 | B2 | 4/2002 | Seitz et al. ................. 544/214 |
| 6,407,097 | B1 | 6/2002 | Gayer et al. ............. 514/222.5 |
| 6,407,233 | B1 | 6/2002 | Heinemann et al. .......... 544/65 |
| 2001/0018442 | A1 | 8/2001 | Gayer et al. ................ 514/269 |
| 2002/0006958 | A1 | 1/2002 | Seitz et al. ................. 514/353 |
| 2002/0028811 | A1 | 3/2002 | Heinemann et al. ........ 514/241 |

FOREIGN PATENT DOCUMENTS

| DE | 196 02 095 | 7/1997 |
| DE | 196 42 533 | 4/1998 |
| EP | 0 794 177 | 9/1997 |
| EP | 0 902 020 | 3/1999 |
| WO | 95/05367 | 2/1995 |
| WO | 98/23155 | 6/1998 |

Primary Examiner—John M. Ford
(74) Attorney, Agent, or Firm—Richard E. L. Henderson

(57) ABSTRACT

The invention relates to a novel process for preparing known asymmetrical 4,6-bis(aryloxy)pyrimidine derivatives.

11 Claims, No Drawings

METHOD FOR PRODUCING ASYMMETRICAL 4,6-BIS(ARYLOXY) PYRIMIDINE DERIVATIVES

The present patent application is filed under 35 U.S.C. 371 for International Application PCT/EPO1/02731, filed Mar. 12, 2001, which was published in German as International Patent Publication WO 01/72719 on Oct. 4, 2001, which is entitled to the right of priority of German Patent Application DE 100 14 607.4, filed Mar. 24, 2000.

The invention relates to a novel process for preparing known asymmetric 4,6-bis(aryloxy)pyrimidine derivatives.

Asymmetric 4,6-bis(aryloxy)pyrimidine derivatives are known and are used, for example, as pesticides in crop protection (cf. WO 94/02470, WO 97/27189, WO 98/21189, WO 99/57116).

The preparation of asymmetric 4,6-bis(aryloxy) pyrimidine derivatives is more difficult than the preparation of symmetric 4,6-bis(aryloxy)pyrimidine compounds since the different aryloxy groups have to be introduced in separate reactions.

A plurality of processes for preparing asymmetric 4,6-bis(aryloxy)pyrimidine derivatives has already been disclosed.

WO 94/02470 describes the preparation of asymmetric 4,6-bis(aryloxy)pyrimidine derivatives by a two-step process. Reaction of 4,6-dichloropyrimidine (A) with one equivalent of a phenol derivative (B) under basic reaction conditions and subsequent reaction with a second phenol derivative (D) gives asymmetric 4,6-bis(aryloxy)pyrimidine derivatives (E) (cf. Scheme 1).

Scheme 1

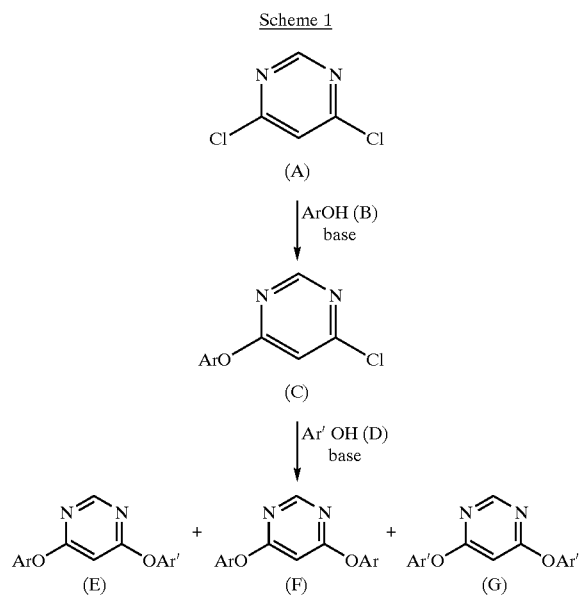

This process has the disadvantage that an exchange of the aryloxy groups takes place in the second reaction step, giving a product mixture of asymmetric 4,6-bis(aryloxy) pyrimidine derivatives (E) and the symmetric 4,6-bis(aryloxy)pyrimidine derivatives (F) and (G).

As a consequence, the asymmetric 4,6-bis(aryloxy) pyrimidine derivatives (E) are obtained in poor yield and can only be isolated by complicated separation methods.

To avoid the problem of the exchange of the aryloxy groups to the second reaction step, it is possible to use the starting material 4,6-difluoropyrimidine (cf. Scheme 2 and WO 94/02470, EP-A1-794 177).

Scheme 2

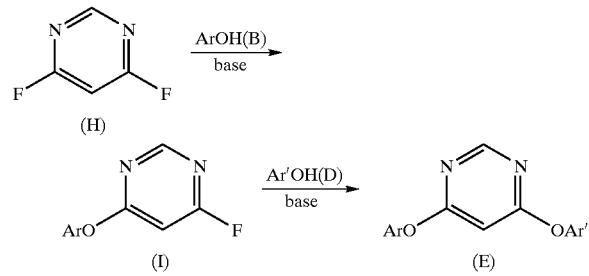

However, this process has the disadvantage that 4,6-difluoropyrimidine has to be prepared by a chlorine/fluorine exchange, starting from 4,6-dichloro-pyrimidine. The preparation of asymmetric 4,6-bis(aryloxy)pyrimidine derivatives therefore requires an additional reaction step. Preferred starting materials are therefore 4,6-dichloropyrimidine or 4,6-dichloropyrimidine derivatives.

The preparation of asymmetric 4,6-bis(aryloxy) pyrimidine derivatives starting from 4,6-dichloro-5-halogeno-pyrimidine analogously, to the process described in WO 94/02470 is described in WO 98/41513.

EP-A1-794 177, U.S. Pat. Nos. 5,849,910 and 5,977,363 describe a further process for preparing asymmetric 4,6-bis(aryloxy)pyrimidine derivatives (E) starting from 4,6-dichloropyrimidine (A) (cf. Scheme 3).

Scheme 3

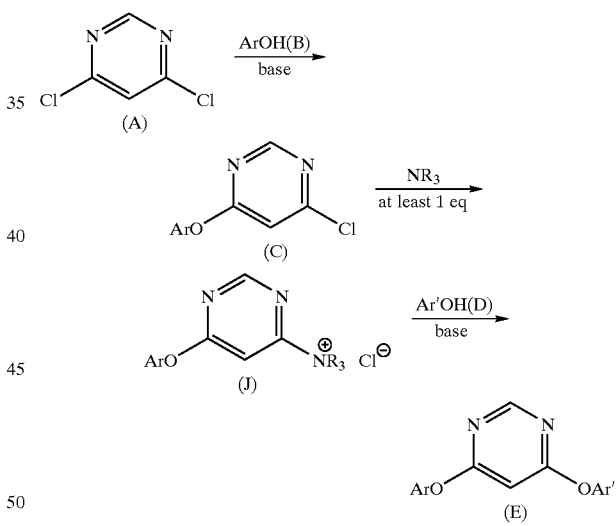

In this process, the aryloxy-chloropyrimidine derivative (C) obtained after the first reaction step is treated with at least one molar equivalent of a tertiary amine.

The intermediates formed are pyrimidinyl-ammonium derivatives (J), which are reacted with phenol derivatives (D) to give asymmetrical 4,6-bis(aryloxy)pyrimidine derivatives (E).

This process has the disadvantage that at least equivalent molar amounts of the tertiary amine are required, which can only be recovered using complicated procedures. Moreover, the asymmetric 4,6-bis(aryloxy)pyrimidine derivatives are only obtained in moderate yields. This process is therefore unsuitable for the large-scale industrial preparation, especially if expensive amines are used.

It has now been found that asymmetric 4,6-bis(aryloxy) pyrimidine derivatives of the general formula (I),

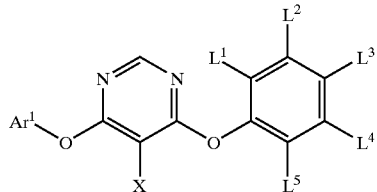

in which

Ar¹ represents in each case substituted or unsubstituted aryl or heterocyclyl,

X represents hydrogen, fluorine, chlorine or bromine,

L¹, L², L³, L⁴ and L⁵ are identical or different and independently of one another each represents hydrogen, halogen, cyano, nitro, alkylcarbonyl formyl, alkoxycarbonyl, aminocarbonyl, alkylaminocarbonyl, dialkylaminocarbonyl, in each case optionally halogen-substituted alkyl, alkoxy, alkylthio, alkylsulphinyl or alkylsulphonyl, or L¹, L², L³ and L⁴ are identical or different and independently of one another each represents hydrogen, halogen, cyano, nitro, alkylcarbonyl, formyl, alkoxycarbonyl, aminocarbonyl, alkylaminocarbonyl, dialkylaminocarbonyl, in each case optionally halogen-substituted alkyl, alkoxy, alkylthio, alkylsulphinyl or alkylsulphonyl, and L⁵ represents one of the groups below:

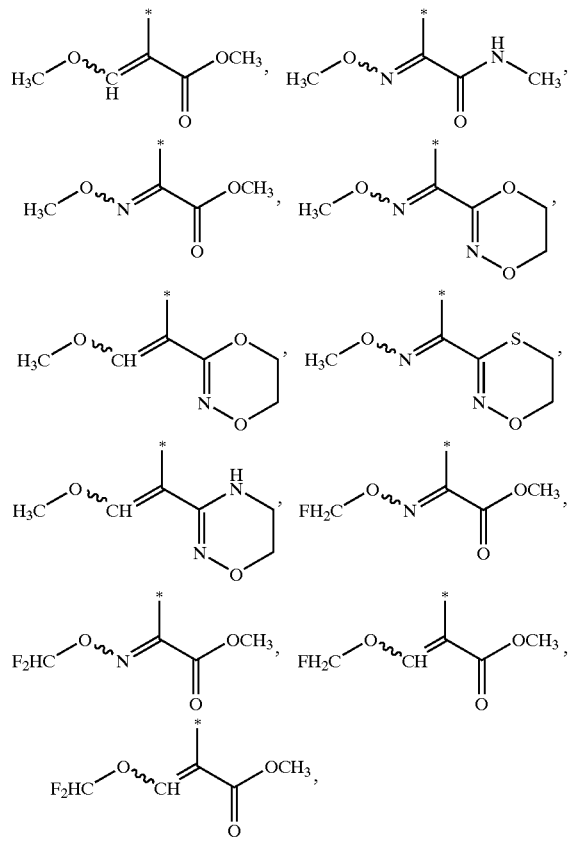

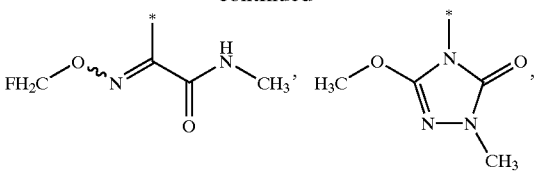

where * denotes the point of attachment to the phenyl radical, and where the radicals

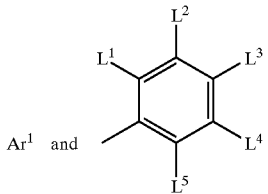

are different, are obtained when 4,6-dichloropyrimidine derivatives of the general formula (II),

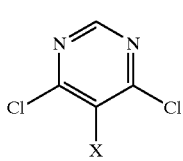

in which

X is as defined above,
a) are initially, in a first step, reacted with compounds of the general formula (III),

in which

Ar¹ is as defined above, if appropriate in the presence of a diluent and if appropriate in the presence of an acid acceptor, and the resulting compounds of formula (IV),

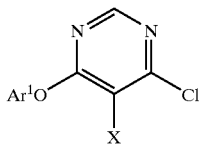

in which

Ar¹ and X are each as defined above are then, in a second step, reacted with compounds of the general formula (V),

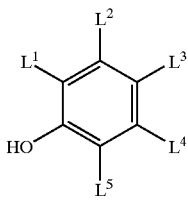
(V)

in which
L¹, L², L³, L⁴ and L⁵ are each as defined above,
if appropriate in the presence of a solvent, if appropriate in the presence of a base and with addition of from 2 to 40 mol % of 1,4-diazabicyclo[2.2.2]octane (DABCO),
or
b) are initially, in a first step, reacted with compounds of the general formula (V),

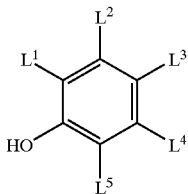
(V)

in which
L¹, L², L³, L⁴ and L⁵ are each as defined above,
if appropriate in the presence of a diluent and if appropriate in the presence of an acid acceptor,
and the resulting compounds of the formula (VI),

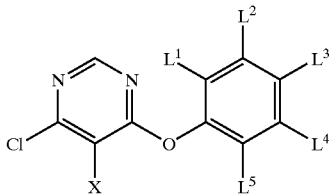
(VI)

in which
X, L¹, L², L³, L⁴ and L⁵ are each as defined above,
are then, in a second step, reacted with compounds of general formula (III), Ar¹—OH, (III)

in which
Ar¹ is as defined above,
if appropriate in the presence of a solvent, if appropriate in the presence of a base and with addition of from 2 to 40 mol % of 1,4-diazabicyclo[2.2.2]octane (DABCO).

In the definitions, the saturated or unsaturated hydrocarbon chains, such as alkyl, alkanediyl, alkenyl or alkinyl, are in each case straight-chain or branched, including in combination with heteroatoms, such as, for example, in alkoxy, alkylthio or alkylamino. Unless indicated otherwise, preference is given to hydrocarbon chains having 1 to 6 carbon atoms. Unless indicated otherwise, hydrocarbon chains having 2 to 6 carbon atoms are preferred for alkenyl or alkinyl.

Halogen generally represents fluorine, chlorine, bromine or iodine, preferably fluorine, chlorine or bromine, in particular fluorine or chlorine.

Aryl represents aromatic, mono- or polycyclic hydrocarbon rings, such as, for example, phenyl, naphthyl, anthranyl, phenanthryl, preferably phenyl or naphthyl, in particular phenyl.

Heterocyclyl represents saturated or unsaturated, and also aromatic, cyclic compounds where at least one ring member is a heteroatom, i.e. an atom different from carbon. If the ring contains a plurality of heteroatoms, this can be identical or different. Preferred heteroatoms are oxygen, nitrogen or sulphur. If the ring contains a plurality of oxygen atoms, these are adjacent. If appropriate, the cyclic compounds form a polycyclic ring system together with other carbocyclic or heterocyclic, fused-on or bridged rings. Preference is given to mono- or bicyclic ring systems, in particular to mono- or bicyclic aromatic ring systems.

Cycloalkyl represents saturated carbocyclic compounds which, if appropriate, form a polycyclic ring system together with other carbocyclic fused-on or bridged rings.

A polycyclic ring system can be attached to a heterocyclic ring or a fused-on carbocyclic ring. This heterocyclyl group can also be mono- or polysubstituted, preferably by methyl, ethyl or halogen. Preference is given to mono- or bicyclic ring systems, in particular mono- or bicyclic aromatic ring systems.

Halogenoalkoxy represents partially or fully halogenated alkoxy. In the case of polyhalogenated halogenoalkoxy, the halogen atoms can be identical or different. Preferred halogen atoms are fluorine and chlorine, in particular fluorine. If the halogenoalkoxy additionally carries other substituents, the maximum number of halogen atoms possible is reduced to the remaining free valencies. Unless indicated otherwise, preference is given to hydrocarbon chains having 1 to 6 carbon atoms.

Halogenoalkyl represents partially or fully halogenated alkyl. In the case of polyhalogenated halogenoalkyl, the halogen atoms can be identical or different. Preferred halogen atoms are fluorine and chlorine, in particular fluorine. If the halogenoalkyl additionally carries other substituents, the maximum number of halogen atoms possible is reduced to the remaining free valencies. Unless indicated otherwise, preference is given to hydrocarbon chains having 1 to 6 carbon atoms.

The starting materials of the formulae (III) and (V), the intermediates of the formulae (IV) and (VI) and the end products of the general formula (I) can be present as pure isomers of different possible isomeric forms, for example E or Z isomers or, as appropriate, as mixtures of different possible isomeric forms, in particular of heteroisomers, such as for example, E/Z mixtures.

In general, Ar¹ represents, in particular:
heterocyclyl having 3 to 7 ring members which is optionally substituted by halogen or by alkyl, alkoxy, halogenoalkyl, halogenoalkoxy having in each case 1 to 4 carbon atoms;
or represents phenyl or naphthyl, each of which is optionally mono- to tetrasubstituted by identical or different substituents, the possible substituents preferably being selected from the list below:
halogen, cyano, nitro, formyl, carboxyl, carbamoyl, thiocarbamoyl;
in each case straight-chain or branched alkyl, oxoalkyl, alkoxy, alkoxyalkyl, alkylthioalkyl, dialkoxyalkyl, alkylthio, alkylsulphinyl or alkylsulphonyl having in each case 1 to 8 carbon atoms;
in each case straight-chain or branched alkenyl or alkenyloxy having in each case 2 to 6 carbon atoms;

in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

in each case straight-chain or branched halogenoalkenyl or halogenoalkenyloxy having in each case 2 to 6 carbon atoms and 1 to 11 identical or different halogen atoms;

in each case straight-chain or branched dialkylamino;

alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl or alkinylcarbonyl, having 1 to 6 carbon atoms in the respective hydrocarbon chain;

cycloalkyl or cycloalkyloxy having in each case from 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which is optionally mono- to tetrasubstituted by identical or different substituents from the group consisting of fluorine, chlorine, oxo, methyl, trifluoromethyl and ethyl;

or a grouping

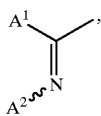

in which $A^1$ represents hydrogen, hydroxyl or alkyl having 1 to 4 carbon atoms or cycloalkyl having 1 to 6 carbon atoms and $A^2$ represents hydroxyl, methoxy, ethoxy, amino, methylamino, phenyl, benzyl or represents in each case optionally cyano-, alkoxy-, alkylthio-, alkylamino-, dialkylamino- or phenyl-substituted alkyl or alkoxy having 1 to 4 carbon atoms, or represents alkenyloxy or alkinyloxy having in each case 2 to 4 carbon atoms, and also phenyl, benzoyl, benzoylethenyl, cinnamoyl, heterocyclyl or phenylalkyl, phenylalkyloxy or heterocyclylalkyl, having in each case 1 to 3 carbon atoms in the respective alkyl moieties and being in each case optionally mono- to trisubstituted in the ring moiety by halogen and/or straight-chain or branched alkyl or alkoxy having 1 to 4 carbon atoms.

Preference is given to compounds in which $Ar^1$ represents:

optionally methyl-, ethyl-, methoxy-, ethoxy-, trifluoromethyl- or trifluoromethoxy-substituted thienyl, pyridyl or furyl;

or represents phenyl which is in each case optionally mono- to tetrasubstituted by identical or different substituents, the possible substituents preferably being selected from the list below:

fluorine, chlorine, bromine, iodine, cyano, nitro, formyl, carboxyl, carbamoyl, thiocarbamoyl, methyl, ethyl, n- or i-propyl, n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimetylbutyl), 1-, 2-(2,3-dimethylbutyl), 3-oxobutyl, methoxymethyl, dimethoxymethyl, methoxy, ethoxy, n- or i-propoxy, methylthio, ethylthio, n- oder i-propylthio, methylsulphinyl, ethylsulphinyl, methylsulphonyl or ethylsulphonyl, vinyl, allyl, 2-methylallyl, propene-1-yl, crotonyl, propargyl, vinyloxy, allyloxy, 2-methylallyloxy, propene-1-yloxy, crotonyloxy, propargyloxy, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, dimethylaminocarbonyloxy, diethylaminocarbonyloxy, benzylaminocarbonyl, acryloyl, propioloyl, cyclopentyl, cyclohexyl, in each case doubly attached propanediyl, ethyleneoxy, each of which is optionally mono- to tetrasubstituted by identical or different substituents from the group consisting of fluorine, chlorine, oxo, methyl and trifluoromethyl, or a grouping

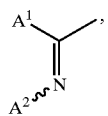

where $A^1$ represents hydrogen, methyl of hydroxyl and $A^2$ represents hydroxyl, methoxy, ethoxy, amino, methylamino, phenyl or benzyl, and also phenyl, benzoyl, benzoylethenyl, cinnamoyl, benzyl, phenylethyl, phenylpropyl, benzyloxy, 5,6-dihydro-1,4,2-dioxazin-3-ylmethyl, triazolylmethyl, benzoxazol-2-ylmethyl, 1,3-dioxan-2-yl, benzimidazol-2-yl, dioxol-2-yl, oxadiazolyl, each of which is optionally mono- to trisubstituted in the ring moiety by halogen and/or straight-chain or branched alkyl or alkoxy having 1 to 4 carbon atoms.

In a further very particularly preferred group of compounds, $Ar^1$ represents mono- to tetrasubstituted phenyl, where the substituents are selected from the list below:

halogen, cyano, in each case straight-chain or branched alkyl or halogenoalkyl having in particular 1 to 4 carbon atoms.

In general, X represents, in particular, fluroine or chlorine.

Particular preference is given to compounds in which X represents fluorine.

In general, $L^1$, $L^2$, $L^3$, $L^4$ and $L^5$ are identical or different and independently of one another each represents in particular hydrogen, halogen, cyano, nitro, formyl, alkylcarbonyl, alkoxycarbonyl, aminocarbonyl, alkylaminocarbonyl, dialkylaminocarbonyl having in each case 1 to 6 carbon atoms, alkyl, alkoxy, alkylthio, alkylsulphinyl or alkylsulphonyl having in each case 1 to 6 carbon atoms and being in each case optionally substituted by 1 to 5 halogen atoms, or $L^1$, $L^2$, $L^3$ and $L^4$ are identical or different and independently of one another each represents in particular hydrogen, halogen, cyano, nitro, formyl, alkylcarbonyl, alkoxycarbonyl, aminocarbonyl, alkylaminocarbonyl, dialkylaminocarbonyl having in each case 1 to 6 carbon atoms, alkyl, alkoxy, alkylthio, alkylsulphinyl or alkylsulphonyl having in each case 1 to 6 carbon atoms and being in each case optionally substituted by 1 to 5 halogen atoms and $L^5$ represents in particular one of the groups below:

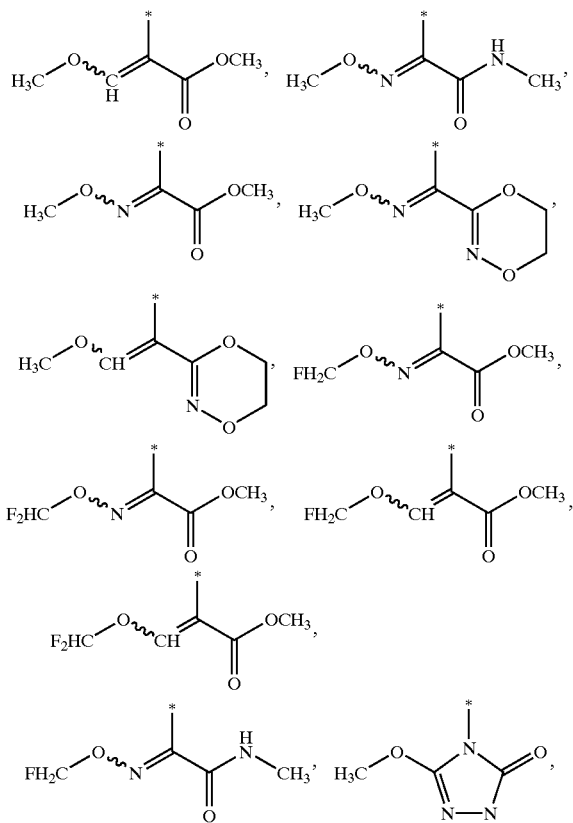

where * denotes the point of attachment to the phenyl radical.

Preference is given to compounds in which $L^1$, $L^2$, $L^3$ and $L^4$ are identical or different and independently of one another each preferably represents hydrogen, fluorine, chlorine, bromine, cyano, nitro, acetyl, propionyl, methoxycarbonyl, ethoxycarbonyl, methylaminocarbonyl, ethylaminocarbonyl, dimethylaminocarbonyl, diethylaminocarbonyl, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

In a very particularly preferred group of compounds, $L^1$, $L^2$, $L^3$ and $L^4$ each represent hydrogen or methyl.

In a further very particularly preferred group of compounds, $L^1$, $L^2$, $L^3$ and $L^4$ each represent hydrogen.

Preference is given to compounds in which $L^5$ represents one of the groups below:

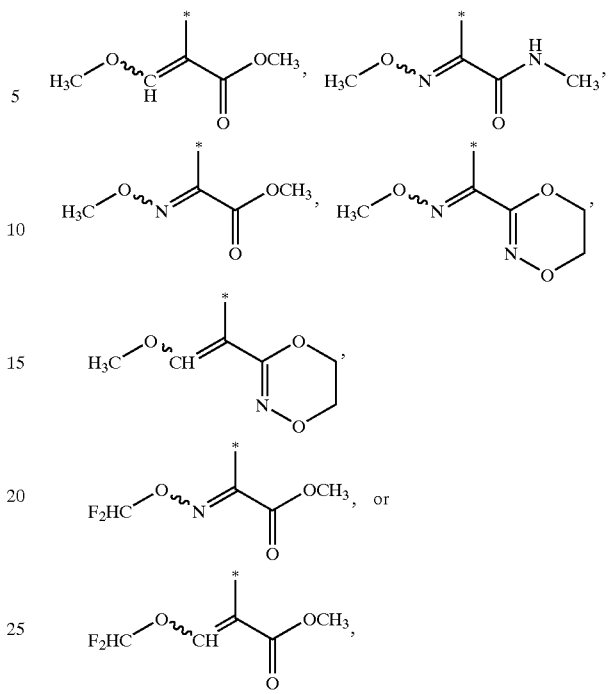

where * denotes the point of attachment to the phenyl radical.

In a very particularly preferred group of compounds, $L^5$ represents one of the groups below:

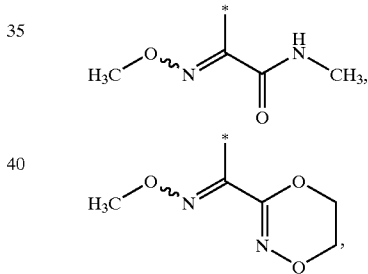

where * denotes the point of attachment to the phenyl radical.

The abovementioned general or preferred radical definitions apply both to the end products of the formula (I) and, correspondingly, to the starting materials or intermediates required in each case for the preparation.

Independently of the combination of radicals given in each case, the definitions of radicals given in the combinations or preferred combinations of radicals in question specifically for these radicals can also be replaced by any definitions of radicals of other preferred ranges.

It is extremely surprising that, in the process according to the invention, aryloxyhalogenopyrimidine derivatives react with high selectivity and yield to give asymmetric 4,6-bis (aryloxy)pyrimidine derivatives when from 2 to 40 mol % of the tertiary amine 1,4-diazabicyclo[2.2.2]octane (DABCO) are added. Since it is mentioned in the prior art (cf. EP-A1-794 177, U.S. Pat. Nos. 5,849,990 and 5,977,363) that this reaction requires at least a molar equivalent of a tertiary amine, it is extremely surprising that this reaction can also be carried out with from 2 to 40 mol % of DABCO, giving excellent yields. This is confirmed by a comparative experiment in which the reaction was carried out without addition of DABCO (cf. Example 4, second step). The product can only be isolated in very poor yields.

The process according to the invention has a number of advantages. The asymmetric 4,6-bis(aryloxy)pyrimidine derivatives are obtained in high yields and purities. Moreover, it is possible to use, as starting materials, 4,6-difluoropyrimidine derivatives, which are easier to obtain than 4,6-dichloropyrimidine derivatives. Traditionally, it is not necessary to recover the amine, since only catalytic amounts of DABCO are needed for carrying out the process.

The compounds of the formula (II) required as starting materials for carrying out the process according to the invention are known and can be prepared by known methods (cf. DE-A1-197 10 609, WO 97/49605, DE-A1-196 42 533 and DE-A1-195 31299) or are commercially available products.

The compounds of the formula (III) required as starting materials for carrying out the process according to the invention are customary commercial products or can be prepared from the latter by simple processes.

The compounds of the formula (V) required as starting materials for carrying out the process according to the invention are known and can be prepared by known methods (cf. DE-A1 196 11 653, WO-A-95/24396, WO 95/04728, WO 97/27189, WO 97/14687, WO 98/23155, WO 98/21189, WO 98/55461, WO 99/09026, WO 99/57116). All other starting materials are customary commercial products or can be prepared from the latter by simple processes.

Suitable diluents for carrying out the first step of the process according to the invention are all inert organic solvents. These include, by way of example and by way of preference, aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl-t-butyl ether, methyl-t-amyl ether, dioxane, tetrahydrofuran, 1,2-dimethoxyethane, 1,2-diethoxyethane or anisole; ketones, such as, for example, acetone, butanone, methyl isobutyl ketone or cyclohexanone, nitriles, such as, for example, acetonitrile, propionitrile, n- or i-butyronitrile or benzonitrile, amides, such as N,N-dimethylformamide, N,N-dimethylacetamide, N-methylformamide, N-methylpyrrolidone or hexamethylphosphoric triamide; esters, such as methyl acetate or ethyl acetate; sulphoxides, such as dimethyl sulphoxide, sulphones, such as sulpholane; or mixtures thereof with water. In the first step of the process according to the invention, preference is given to using ketones, in particular methyl isobutyl ketone.

The first step of the process according to the invention is, if appropriate, carried out in the presence of a suitable acid acceptor. Suitable acid acceptors are all customary inorganic or organic bases. These include, by way of example and by way of preference, alkaline earth metal or alkali metal hydroxides, acetates, carbonates or bicarbonates, such as, for example, sodium hydroxide, potassium hydroxide, sodium acetate, potassium acetate, sodium carbonate, potassium carbonate, potassium bicarbonate or sodium bicarbonate; tertiary amines, such as, for example, trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclononene (DBN) oir diazabicycloundecene (DBU); and also alkaline earth metal or alkali metal hydrides, such as, for example, calcium hydride, sodium hydride or potassium hydride. In the first step of the process according to the invention, preference is given to using alkaline earth metal or alkalimetal carbonates, in particular potassium carbonate or sodium carbonate.

In the first step of the process according to the invention, the reaction temperatures can be varied within a relatively wide range. In general, the reaction is carried out at temperatures from 0° C. to 100° C., preferably at temperatures from 40° C. to 80° C.

For carrying out the process according to the invention, in general from 1 to 4 mol, preferably from 1 to 1.1 mol, of the 4,6-dichloropyrimidine derivatives of the formula (II) are employed per mole of the compounds of the formula (III).

For carrying out the process according to the invention, in general from 1 to 4 mol, preferably from 1 to 1.1 mol, of the 4,6-dichloropyrimidine derivatives of the formula (II) are employed per mole of the compounds of the formula (V).

For carrying out the first step of the process according to the invention, the following procedure is generally adopted. The 4,6-dichloropyrimidine derivative of the formula (II) is, if appropriate in the presence of a diluent, admixed with a base. The compound of the formula (III) or the compound of the formula (V) is added, if appropriate in the presence of a diluent, and the mixture is, if appropriate at elevated or at radius temperature, stirred until the reaction has gone to completion. After the reaction has ended, the reaction mixture is worked up in a customary manner or reacted directly in situ in the second step of the process according to the invention.

The addition of compounds of the formula (III) or of compounds of the formula (V), if appropriate in the presence of diluent, in the first step of the process according to the invention is carried out, in particular, by metered addition to compounds of the formula (II) dissolved, if appropriate, in a ketone, in particular in methyl isobutyl ketone. The addition is carried out all at once or within a period of 12 hours, preferably all at once or within a period of 6 hours.

Suitable diluents for carrying out the second step of the process according to the invention are all inert organic solvents. These include, by way of example and by way of preference, aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as, for example, diethyl ether, diisopropyl ether, methyl-t-butyl ether, methyl-t-amyl ether, dioxane, tetrahydrofuran, 1,2-dimethoxyethane, 1,2-diethoxyethane or anisole; ketones, such as, for example, acetone, butanone, methyl isobutyl ketone or cyclohexanone, nitrites, such as, for example, acetonitrile, propionitrile, n- or i-butyronitrile or benzonitrile, amides, such as N,N-dimethylformanilide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide, sulphones, such as sulpholane; or mixtures thereof with water. In the second step of the process according to the invention, preference is given to using ketones, in particular methyl isobutyl ketone.

The second step of the process according to the invention is, if appropriate, carried out in the presence of a suitable acid acceptor. Suitable acid acceptors are all customary inorganic or organic bases. These include, by way of example and by way of preference, alkaline earth metal or alkali metal hydroxides, acetates, carbonates or bicarbonates, such as sodium hydroxide, potassium hydroxide, sodium acetate, potassium acetate, sodium carbonate, potassium carbonate, potassium bicarbonate or sodium bicarbonate; and also alkaline earth metal or alkali metal hydrides, such as, for example, calcium hydride, sodium hydride or potassium hydride. In the second step of the process according to the invention, preference is given to using alkaline earth metal or alkali metal carbonates, in particular potassium carbonate or sodium carbonate.

The second step of the process according to the invention is carried out in the presence of catalytic amounts of 1,4-diazabicyclo[2.2.2]octane (DABCO).

When carrying out the second step of the process according to the invention, the reaction temperatures can be varied within a relatively wide range. In general, the reaction is carried out at temperatures of from 0° C. to 100° C., preferably at temperatures of from 40° C. to 90° C., in particular at temperatures of from 50° C. to 80° C.

For carrying out the process according to the invention, in general from 0.8 to 4 mol, preferably from 0.95 to 1.05 mol, of the compounds of the formula (V) are employed per mole of the compounds of the formula (IV).

For carrying out the process according to the invention, in general from 0.8 to 4 mol, preferably from 0.95 to 1.05 mol, of the compounds of the formula (III) are employed per mole of the compounds of the formula (VI).

For carrying out the process according to the invention, in general from 2 to 40 mol %, preferably from 2 to 20 mol %, of 1,4-diazabicyclo[2.2.2]octane are employed per mole of the compounds of formula (IV).

For carrying out the process according to the invention, in general from 2 to 40 mol %, preferably from 2 to 20 mol %, of 1,4-diazabicyclo[2.2.2]octane are employed per mole of the compounds of formula (VI).

The second step of process variant a) is generally carried out as follows. The compounds of the formula (V) are, if appropriate in the presence of a diluent, admixed with a base and 1,4-diazabicyclo[2.2.2]octane. The compounds of the formula (IV) are added, if appropriate in the presence of the diluent, and the mixture is stirred, if appropriate at elevated temperature. After the reaction has ended, the reaction mixture is worked up in a customary manner.

Alternatively, the second step of process variant a) can also be carried out by admixing the compounds of the formula (IV), if appropriate in the presence of a diluent, with a base and 1,4-diazabicyclo[2.2.2]octane. The compounds of the formula (V) are added, if appropriate in the presence of a diluent, and the mixture is stirred, if appropriate at elevated temperature. After the reaction has ended, the reaction mixture is worked up in a customary manner.

The second step of process variant b) is generally carried out as follows. The compounds of the formula (III) are, if appropriate in the presence of a diluent, admixed with a base and 1,4-diazabicyclo[2.2.2]octane. The compounds of the formula (VI) are added, if appropriate in the presence of the diluent, and the mixture is stirred, if appropriate at elevated temperature. After the reaction has ended, the reaction mixture is worked up in a customary manner.

Alternatively, process step b) can also be carried out by admixing the compounds of the formula (VI), if appropriate in the presence of a diluent, with a base and 1,4-diazabicyclo[2.2.2]octane. The compounds of the formula (III) are added, if appropriate in the presence of a diluent, and the mixture is stirred, if appropriate at elevated temperature. After the reaction has ended, the reaction mixture is worked up in a customary manner. In a specific variant, the process according to the invention is carried out as a one-pot reaction.

The examples below serve to illustrate the invention. However, the invention is not limited to the examples.

EXAMPLES

Example 1

Process Variant a) or b)

4-Chloro-5-fluoro-6-[4-fluoro-3-(trifluoromethyl)phenoxy]pyrimidine

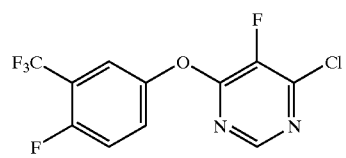

(IV-1)

First Step 4,6-Dichloro-5-fluoropyrimidine (1.67 g, content: 98.9%) and potassium carbonate (1.72 g) are initially charged in methyl isobutyl ketone (5 ml), and the mixture is, at 60° C., admixed dropwise over a period of 3 hours with a solution of 1.8 g of 4-fluoro-3-(trifluoromethyl)phenol in 5 ml of methyl isobutyl ketone. The mixture is stirred at 60° C. for 1.5 hours and then cooled, admixed with water, the organic phase is separated off, the aqueous phase is extracted once more with methyl isobutyl ketone, the organic extracts are combined and dried over sodium sulphate and the solvent is distilled off. This gives 4-chloro-5-fluoro-6-[4-fluoro-3-(trifluoromethyl)phenoxy]pyrimidine (2.74 g, content: 93.9%, 83.8% of theory) as an oil.

4-[4-Chloro-3-(trifluoromethyl)phenoxy]-5-fluoro-6-[4-fluoro-3-(trifluoromethyl)phenoxy]pyrimidine

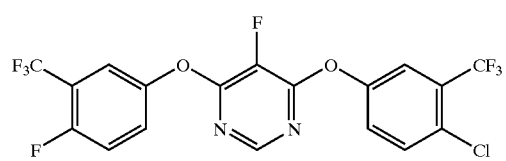

(I-1)

Second Step

4-Chloro-3-(trifluoromethyl)phenol (0.98 g) together with potassium carbonate (0.9 g) and 1,4-diazabicyclo[2.2.2]octane (DABCO) (28 mg), is initially charged in a methyl isobutyl ketone/water mixture (8 ml, 7/1), and, at 70-80° C., admixed with a solution of 4-chloro-5-fluoro-6-[4-fluoro-3-(trifluoromethyl)phenoxy]pyrimidine (1.56 g, content: 98.8%) in 7 ml of methyl isobutyl ketone. The mixture is stirred at 70–80° C. for 2 hours and then cooled, water is added, the organic phase is separated off, the aqueous phase is extracted with methyl isobutyl ketone, the combined organic extracts are dried over sodium sulphate and the solvent is distilled off. This gives 4-[4-chloro-3-(trifluoromethyl)phenoxy]-5-fluoro-6-[4-fluoro-3-(trifluoromethyl)phenoxy]pyrimidine (1.92 g, content: 96.5%, 79.2% of theory) as a solid.

Example 2

Process Variant a)

4-Chloro-6-(3-chloro-2-methylphenoxy)-5-fluoropyrimidine

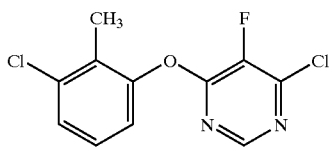

(IV-2)

First Step 4,6-Dichloro-5-fluoropyrimidine (16,7 g, content: 99.7%) and potassium carbonate (20.2 g) are initially charged in methyl isobutyl ketone (50 ml), and, at 60° C., admixed dropwise over a period of 3.5 hours with a solution of 14.3 g of 3-chloro-2-methylphenol in 50 ml of methyl isobutyl ketone. The mixture is stirred at 60° C. for 2 hours and then cooled, admixed with water, the organic phase is separated off, the aqueous phase is extracted once more with methyl isobutyl ketone, the organic extracts are combined and dried over sodium sulphate and the solvent is distilled off. This gives 4-chloro-6-(3-chloro-2-methylphenoxy)-5-fluoropyrimidine (26.8 g, content: 96.7%, 95.2% of theory) as a solid.

(2E)-2-(2-{[6-(3-Chloro-2-methylphenoxy)-5-fluoro-4-pyrimidinyl]oxy}phenyl)-2-(methoxyimino)-N-methylethanamide

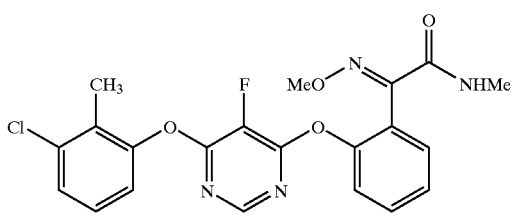

(I-2)

Second Step (2E)-2-(2-Hydroxyphenyl)-2-(methoxyimino)-N-methylethanamide (4.16 g, content: 99.7%), together with potassium carbonate (3.7 g) and DABCO (110 mg), is initially charged in methyl isobutyl ketone (30 ml), and, at 50° C., admixed with a solution of 4-chloro-6-(3-chloro-2-methylphenoxy)-5-fluoropyrimidine (5.46 g, content: 98.1%) in 30 ml of methyl isobutyl ketone. The mixture is stirred at 50° C. for 4 hours and then cooled, water is added, the organic phase is separated off, the aqueous phase is extracted with methyl isobutyl ketone, the combined organic extracts are dried over sodium sulphate and the solvent is distilled off. This gives (2E)-2-(2-{[6-(3-chloro-2-methylphenoxy)-5-fluoro-4-pyrimidinyl]oxy}phenyl)-2-(methoxyimino)-N-methylethanamide (9.15 g, content: 94.2%, 96.9% of theory) as an oil.

Example 3

Process Variant a)

4-Chloro-6-(2-chlorophenoxy)-5-fluoropyrimidine

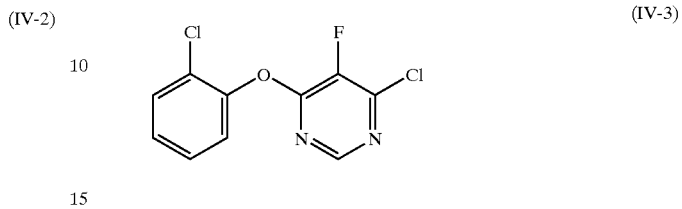

(IV-3)

First Step 4,6-Dichloro-5-fluoropyrimidine (33.5 g, content: 98.9%) and potassium carbonate (34.4 g) are initially charged in a methyl isobutyl ketone/water mixture (120 ml, 5/1) and, at 60° C., admixed dropwise over a period of 3 hours with a solution of 25.7 g of o-chlorophenol in 100 ml of methyl isobutyl ketone. The mixture is stirred at 60° C. for 6 hours and then cooled, the organic phase is separated off and washed with 5% NaOH, the aqueous phase is extracted with methyl isobutyl ketone, the organic extracts are combined and dried over sodium sulphate and the solvent is distilled off. This gives 4-chloro-6-(2-chlorophenoxy)-5-fluoropyrimidine (48.4 g, content: 95.6%, 90.3% of theory) as an oil.

(E)-(2-{[6-(2-Chlorophenoxy)-5-fluoro-4-pyrimidinyl]oxy}phenyl)-(5,6-dihydro-1,4,2-dioxazin-3-yl)methanone O-methyloxime

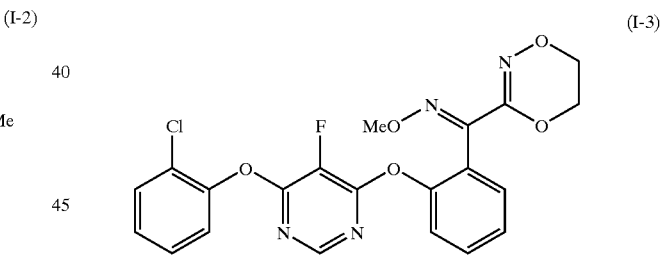

(I-3)

Second Step (E)-5,6-Dihydro-1,4,2-dioxazin-3-yl-(2-hydroxyphenyl)methanone O-methyloxime (11.8 g), together with potassium carbonate (9.0 g) and DABCO (280 mg), is initially charged in a methyl isobutyl ketone/water mixture (80 ml, 7/1) and, at 80° C., admixed with a solution of 4-chloro-6-(2-chlorophenoxy)-5-fluoropyrimidine (13.1 g, content: 98.1%) in 70 ml of methyl isobutyl ketone. The mixture is stirred at 80° C. for 1.5 hours and then cooled, water is added, the organic phase is separated off, the aqueous phase is extracted with methyl isobutyl ketone, the combined organic extracts are dried over sodium sulphate and the solvent is distilled off. This gives (E)-2-(2-{[6-(2-chlorophenoxy)-5-fluoro-4-pyrimidinyl]oxy}phenyl)-(5,6-dihydro-1,4,2-dioxazin-3-yl)methanone O-methyloxime (23.4 g, content: 95.2%, 97.9% of theory) as a solid.

Example 4

Process Variant a)

4-Chloro-6-(2-chlorophenoxy)-5-fluoropyrimidine

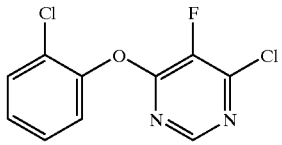

(IV-3)

First Step 4,6-Dichloro-5-fluoropyrimidine (33.5 g, content: 98.9%) and potassium carbonate (34.4 g) are initially charged in a methyl isobutyl ketone/water mixture (120 ml, 5/1), and, at 60° C., admixed dropwise over a period of 3 hours with a solution of 25.7 g of o-chlorophenol in 100 ml of methyl isobutyl ketone. The mixture is stirred at 60° C. for 6 hours and then cooled, the organic phase is separated off and washed with 5% NaOH, the aqueous phase is extracted with methyl isobutyl ketone, the organic extracts are combined and dried over sodium sulphate and the solvent is distilled off. This gives 4-chloro-6-(2-chlorophenoxy)-5-fluoropyrimidine (48.4 g, content: 95.6%, 90.3% of theory) as an oil.

(E)-(2-{[6-(2-Chlorophenoxy)-5-fluoro-4-pyrimidinyl]oxy}phenyl)-(5,6-dihydro-1,4,2-dioxazin-3-yl)methanone O-methyloxime

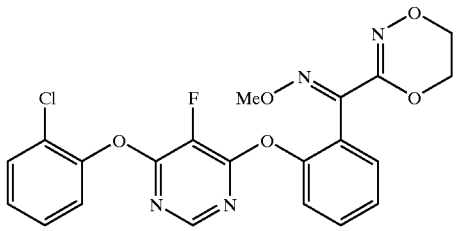

(I-3)

Second Step, Comparative Experiment (E)-5,6-Dihydro-1,4,2-dioxazin-3-yl-(2-hydroxyphenyl)methanone O-methyloxime (11.8 g) and potassium carbonate (9.0 g) are initially charged in a methyl isobutyl ketone/water mixture (80 ml, 7/1), and, at 50° C., admixed with a solution of 4-chloro-6-(2-chlorophenoxy)-5-fluoropyrimidine (13.1 g, content: 98.1%) in 70 ml of methyl isobutyl ketone. The mixture is stirred at 50° C. for 24 hours and then cooled, water is added, the organic phase is separated off, the aqueous phase is extracted with methyl isobutyl ketone, the combined organic extracts are dried over sodium sulphate and the solvent is distilled off. This gives (E)-2-(2-{[6-(2-chlorophenoxy)-5-fluoro-4-pyrimidinyl]oxy}phenyl)-(5,6-dihydro-1,4,2-dioxazin-3-yl)methanone O-methyloxime (26.4 g, content: 33.3%, 38.6% of theory) as an oil.

Example 5

Process Variant b)

(E)-{2-[(6-Chloro-5-fluoro-4-pyrimidinyl)oxy]phenyl}(5,6-dihydro-1,4,2,-dioxazin-3-yl)methanone O-methyloxime

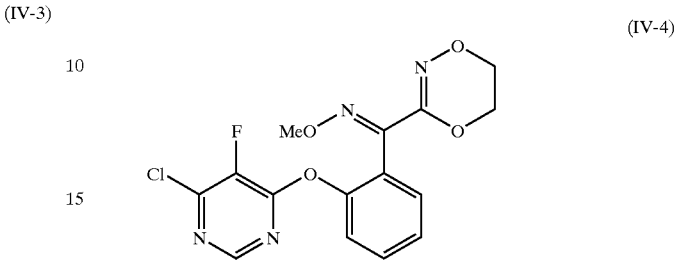

(IV-4)

First Step 4,6-Dichloro-5-fluoropyrimidine (31.8 g, content: 98.9%) and potassium carbonate (31.5 g) are initially charged in acetone (115 ml), and, at 60° C., admixed dropwise over a period of 6 hours with a solution of 44.9 g of (E)-5,6-dihydro-1,4,2-dioxazin-3-yl-(2-hydroxyphenyl)methanone O-methyloxime in 350 ml of acetone. The mixture is stirred at 60° C. for 2 hours, the acetone is distilled off, the mixture is admixed with methylene chloride and water, the organic phase is separated off, the aqueous phase is extracted with methylene chloride, the organic extracts are combined, washed with 5% NaOH and dried over sodium sulphate and the solvent is distilled off. This gives (E)-{2-[(6-chloro-5-fluoro-4-pyrimidinyl)oxy]phenyl}-(5,6-dihydro-1,4,2,-dioxazin-3-yl)methanone O-methyloxime (68.0 g, content: 95.8%, 94.5% of theory) as a solid.

What is claimed is:
1. A process for preparing a compound of formula (I):

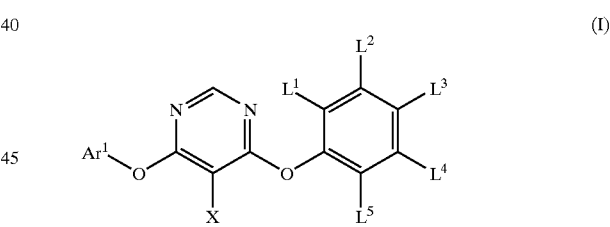

(I)

in which

Ar$^1$ represents substituted or unsubstituted aryl or heterocyclyl,

X represents hydrogen, fluorine, chlorine, or bromine,

L$^1$, L$^2$, L$^3$, and L$^4$ are identical or different and independently of one another represent hydrogen, halogen, cyano, nitro, alkylcarbonyl, formyl, alkoxycarbonyl, aminocarbonyl, alkylaminocarbonyl, dialkylaminocarbonyl, or optionally halogen-substituted alkyl, alkoxy, alkylthio, alkylsulphinyl, or alkylsulphonyl, and L$^5$ represents hydrogen, halogen, cyano, nitro, alkylcarbonyl, formyl, alkoxycarbonyl, aminocarbonyl, alkylaminocarbonyl, dialkylaminocarbonyl, or optionally halogen-substituted alkyl, alkoxy, alkylthio, alkylsuiphinyl, or alkylsulphonyl, or represents one of the groups:

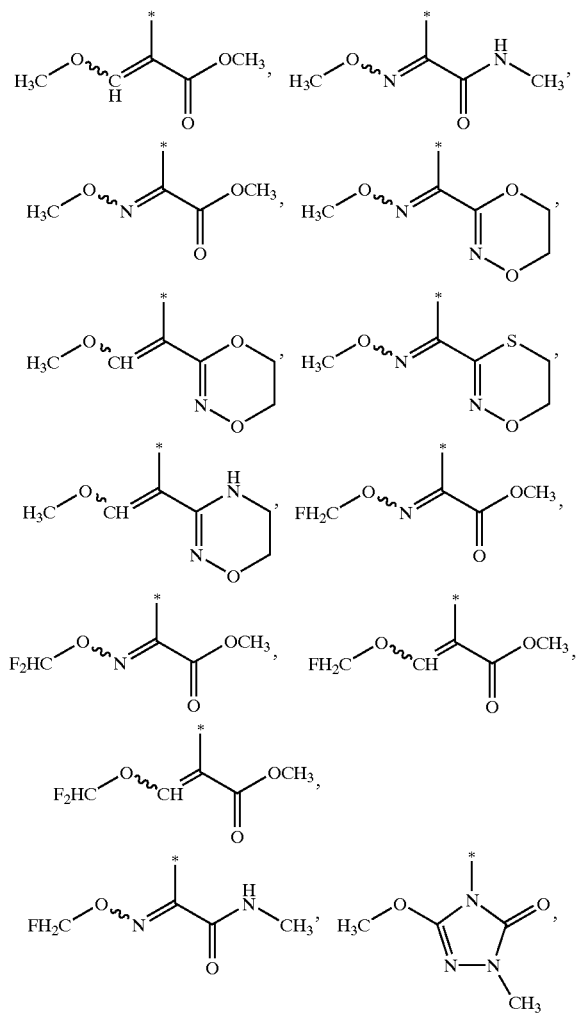

where * denotes the point of attachment to the phenyl radical of formula (I), with the proviso that the radicals:

Ar¹ and

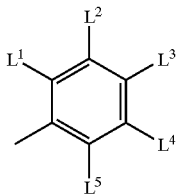

are different from each other, comprising reacting a 4,6-dichloropyrimidine derivative of formula (II):

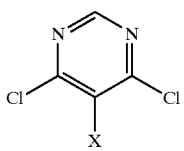

(II)

in which X is as defined for formula (I), either (a) in a first step, with a compound of formula (III):

Ar¹—OH,     (III)

in which Ar¹ is as defined for formula (I), optionally in the presence of a diluent and optionally in the presence of an acid acceptor, to form a compound of formula (IV):

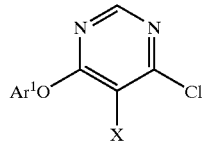

(IV)

in which Ar¹ and X are each as defined for formula (I), and in a second step, reacting the compound of formula (IV) with a compound of formula (V):

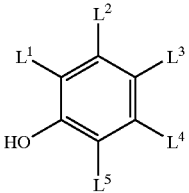

(V)

in which $L^1$, $L^2$, $L^3$, $L^4$, and $L^5$ are each as defined for formula (I), with addition of from 2 to 40 mol % of 1,4-diazabicyclo[2.2.2]octane, optionally in the presence of a solvent and optionally in the presence of a base, or (b) in a first step, with a compound of formula (V):

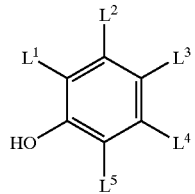

(V)

in which $L^1$, $L^2$, $L^3$, $L^4$, and $L^5$ are each as defined for formula (I), optionally in the presence of a diluent and optionally in the presence of an acid acceptor, to form a compound of formula (VI):

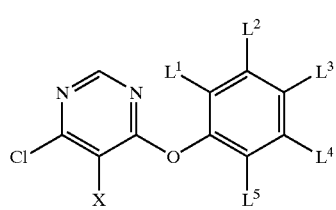

(VI)

in which X, $L^1$, $L^2$, $L^3$, $L^4$, and $L^5$ are each as defined for formula (I), and in a second step, reacting the compound of formula (VI) with a compound of formula (III):

Ar¹—OH,     (III)

in which Ar¹ is as defined for formula (I), with addition of from 2 to 40 mol % of 1,4-diazabicyclo[2.2.2]octane, optionally in the presence of a solvent and optionally in the presence of a base.

2. A process according to claim 1 wherein from 2 to 20 mol % of 1,4-diazabicyclo[2.2.2]octane are used per mole of the compound of formula (IV).

3. A process according to claim 1 wherein from 2 to 20 mol % of 1,4-diazabicyclo[2.2.2]octane are used per mole of the compound of formula (VI).

4. A process according to claim 1 carried out as a one-pot process.

5. A process according to claim 1 wherein from 1 to 4 mol of the 4,6-dichloropyrimidine derivative of formula (II) are employed per mole of the compound of formula (III).

6. A process according to claim 1 wherein from 1 to 4 mol of the 4,6-dichloropyrimidine derivative of formula (II) are employed per mole of the compound of formula (V).

7. A process according to claim 1 wherein from 0.8 to 4 mol of the compound of formula (V) are employed per mole of the compound of formula (IV).

8. A process according to claim 1 wherein from 0.8 to 4 mol of the compound of formula (III) are employed per mole of the compound of formula (VI).

9. A process according to claim 1 wherein $Ar^1$ represents:
  (i) heterocyclyl having 3 to 7 ring members that is optionally substituted by halogen or by alkyl, alkoxy, halogenoalkyl, or halogenoalkoxy having in each case 1 to 4 carbon atoms; or
  (ii) phenyl or naphthyl, each of which is optionally mono- to tetra-substituted by identical or different substituents selected from the group consisting of
    (1) halogen, cyano, nitro, formyl, carboxyl, carbamoyl, or thiocarbamoyl;
    (2) straight-chain or branched alkyl, oxoalkyl, alkoxy, alkoxyalkyl, alkylthioalkyl, dialkoxyalkyl, alkylthio, alkylsulphinyl, or alkylsulphonyl having in each case 1 to 8 carbon atoms;
    (3) straight-chain or branched alkenyl or alkenyloxy having in each case 2 to 6 carbon atoms;
    (4) straight-chain or branched halogenoalkyl, halogenoalkoxy, halogenoalkylthio, halogenoalkylsulphinyl, or halogenoalkylsulphonyl having in each case 1 to 6 carbon atoms and 1 to 13 identical or different halogen atoms;
    (5) straight-chain or branched halogenoalkenyl or halogeno-alkenyloxy having in each case 2 to 6 carbon atoms and 1 to 11 identical or different halogen atoms;
    (6) straight-chain or branched dialkylamino;
    (7) alkylcarbonyl, alkylcarbonyloxy, alkoxycarbonyl, alkylamino-carbonyl, dialkylaminocarbonyl, arylalkylaminocarbonyl, dialkylaminocarbonyloxy, alkenylcarbonyl, or alkinylcarbonyl, having 1 to 6 carbon atoms in the respective hydrocarbon chain;
    (8) cycloalkyl or cycloalkyloxy having in each case from 3 to 6 carbon atoms;
    (9) doubly attached alkylene having 3 or 4 carbon atoms, oxyalkylene having 2 or 3 carbon atoms, or dioxyalkylene having 1 or 2 carbon atoms, each of which is optionally mono- to tetrasubstituted by identical or different substituents selected from the group consisting of fluorine, chlorine, oxo, methyl, trifluoromethyl, and ethyl; and

(10) a grouping

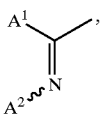

in which:

$A^1$ represents hydrogen, hydroxyl or alkyl having 1 to 4 carbon atoms, or cycloalkyl having 1 to 6 carbon atoms, and $A^2$ represents hydroxyl, methoxy, ethoxy, amino, methylamino, phenyl, or benzyl; optionally cyano-, alkoxy-, alkylthio-, alkylamino-, dialkylamino-, or phenyl-substituted alkyl or alkoxy having 1 to 4 carbon atoms; alkenyloxy or alkinyloxy having in each case 2 to 4 carbon atoms; or phenyl, benzoyl, benzoylethenyl, cinnamoyl, heterocyclyl or phenylalkyl, phenylalkyloxy, or heterocyclylalkyl, having in each case 1 to 3 carbon atoms in the respective alkyl moieties and being in each case optionally mono- to trisubstituted in the ring moiety by halogen and/or straight-chain or branched alkyl or alkoxy having 1 to 4 carbon atoms, X represents fluorine or chlorine, $L^1, L^2, L^3$, and $L^4$ are identical or different and independently of one another represent hydrogen, halogen, cyano, nitro, formyl; alkylcarbonyl, alkoxy-carbonyl, aminocarbonyl, alkylaminocarbonyl, dialkylaminocarbonyl having in each case 1 to 6 carbon atoms; or alkyl, alkoxy, alkylthio, alkylsulphinyl, or alkylsuiphonyl having in each case 1 to 6 carbon atoms and being in each case optionally substituted by 1 to 5 halogen atoms, and $L^5$ hydrogen, halogen, cyano, nitro, formyl; alkylcarbonyl, alkoxycarbonyl, aminocarbonyl, alkylaminocarbonyl, dialkylaminocarbonyl having in each case 1 to 6 carbon atoms; or alkyl, alkoxy, alkylthio, alkylsuiphinyl, or alkylsulphonyl having in each case 1 to 6 carbon atoms and being in each case optionally substituted by 1 to 5 halogen atoms; or represents one of the groups:

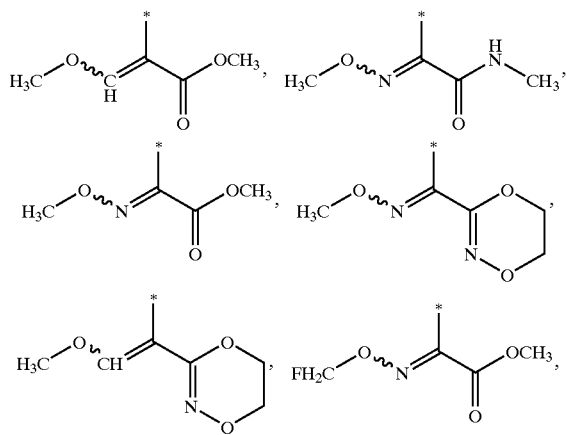

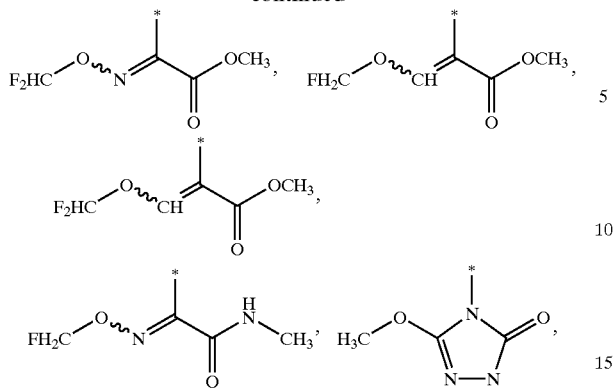

where * denotes the point of attachment to the phenyl radical of formula (I).

10. A process according to claim 1 wherein

Ar$^1$ represents
(i) optionally methyl-, ethyl-, methoxy-, ethoxy-, trifluoromethyl-, or trifluoromethoxy-substituted thienyl, pyridyl, or furyl;
(ii) phenyl that is optionally mono- to tetrasubstituted by identical or different substituents selected from the group consisting of fluorine, chlorine, bromine, iodine, cyano, nitro, formyl, carboxyl, carbamoyl, thiocarbamoyl, methyl, ethyl, n- or i-propyl, n-, i-, s-, or t-butyl, 1-, 2-, 3-, or neo-pentyl, 1-, 2-, 3-, or 4-(2-methylbutyl), 1-, 2-, or 3-hexyl, 1-, 2-, 3-, 4-, or 5-(2-methylpentyl), 1-, 2-, or 3-(3-methylpentyl), 2-ethylbutyl, 1-, 3-, or 4-(2,2-dimethylbutyl), 1- or 2-(2,3-dimethylbutyl), 3-oxobutyl, methoxymethyl, dimethoxymethyl, methoxy, ethoxy, n- or i-propoxy, methylthio, ethylthio, n- or i-propylthio, methylsulphinyl, ethylsulphinyl, methylsulphonyl, ethylsulphonyl, vinyl, allyl, 2-methylallyl, propene-1-yl, crotonyl, propargyl, vinyloxy, allyloxy, 2-methylallyloxy, propene-1-yloxy, crotonyloxy, propargyloxy, trifluoromethyl, trifluoroethyl, difluoromethoxy, trifluoromethoxy, difluorochloromethoxy, trifluoroethoxy, difluoromethylthio, trifluoromethylthio, difluorochloro-methylthio, trifluoromethylsulphinyl, trifluoromethylsulphonyl, dimethylamino, diethylamino, acetyl, propionyl, methoxycarbonyl, ethoxycarbonyl, methylaminocarbonyl, ethylaminocarbonyl, dimethyl-aminocarbonyl, diethylaminocarbonyl, dimethylaminocarbonyloxy, diethylaminocarbonyloxy, benzylaminocarbonyl, acryloyl, propioloyl, cyclopentyl, cyclohexyl, doubly attached propanediyl or ethyleneoxy, each of which is optionally mono- to tetrasubstituted by identical or different substituents from the group consisting of fluorine, chlorine, oxo, methyl, and trifluoromethyl, and a grouping

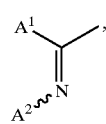

where

A$^1$ represents hydrogen, methyl or hydroxyl and

A$^2$ represents hydroxyl, methoxy, ethoxy, amino, methylamino, phenyl, or benzyl; or phenyl, benzoyl, benzoylethenyl, cinnamoyl, benzyl, phenylethyl, phenylpropyl, benzyloxy, 5,6-dihydro-1,4,2-dioxazin-3-ylmethyl, triazolylmethyl, benzoxazol-2-ylmethyl, 1,3-dioxan-2-yl, benzimidazol-2-yl, dioxol-2-yl, or oxadiazolyl, each of which is optionally mono- to trisubstituted in the ring moiety by halogen and/or straight-chain or branched alkyl or alkoxy having 1 to 4 carbon atoms, X represents fluorine, L$^1$, L$^2$, L$^3$, and L$^4$ are identical or different and independently of one another represent hydrogen, fluorine, chlorine, bromine, cyano, nitro, acetyl, propionyl, methoxycarbonyl, ethoxycarbonyl, methylaminocarbonyl, ethylaminocarbonyl, dimethylaminocarbonyl, diethylaminocarbonyl, methyl, ethyl, n- or i-propyl, n-, i-, s-, or t-butyl, methoxy, ethoxy, n- or i-propoxy, methylthio, ethylthio, methylsulphinyl, ethylsulphinyl, methylsulphonyl, ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, or trifluoromethylsulphonyl, and L$^5$ represents one of the groups:

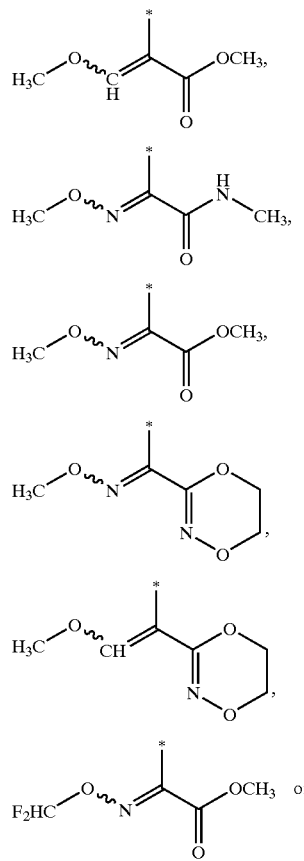

-continued

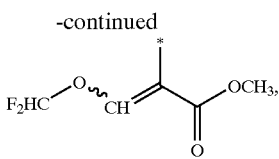

where * denotes the point of attachment to the phenyl radical of formula (I).

11. A process according to claim 1 wherein
Ar¹ represents:
(i) optionally methyl-, ethyl-, methoxy-, ethoxy-, trifluoromethyl-, or trifluoromethoxy-substituted thienyl, pyridyl, or furyl; or
(ii) phenyl that is optionally mono- to tetrasubstituted by identical or different substituents selected from the group consisting of fluorine, chlorine, bromine, iodine, cyano, nitro, formyl, carboxyl, carbamoyl, thiocarbamoyl, methyl, ethyl, n- or i-propyl, n-, i-, s-, or t-butyl, 1-, 2-, 3-, or neo-pentyl, 1-, 2-, 3-, or 4-(2-methylbutyl), 1-, 2-, or 3-hexyl, 1-, 2-, 3-, 4-, or 5-(2-methylpentyl), 1-, 2-, or 3-(3-methylpentyl), 2-ethylbutyl, 1-, 3-, 4-(2,2-dimethylbutyl), 1- or 2-(2,3-dimethylbutyl), 3-oxobutyl, methoxymethyl, dimethoxymethyl, methoxy, ethoxy, n- or i-propoxy, methylthio, ethylthio, n- or i-propylthio, methylsulphinyl, ethylsulphinyl, methylsulphonyl, ethylsulphonyl, vinyl, allyl, 2-methylallyl, propene-1-yl, crotonyl, propargyl, vinyloxy, allyloxy, 2-methylallyloxy, propene-1-yloxy, crotonyloxy, propargyloxy, trifluoromethyl, trifluoroethyl, difluoromethoxy, trifluoromethoxy, difluorochloromethoxy, trifluoroethoxy, difluoromethylthio, trifluoromethylthio, difluorochloro-methylthio, trifluoromethylsulphinyl or trifluoromethylsulphonyl, dimethylamino, diethylamino, acetyl, propionyl, methoxycarbonyl, ethoxycarbonyl, methylaminocarbonyl, ethylaminocarbonyl, dimethylaminocarbonyl, diethylaminocarbonyl, dimethylamino-carbonyloxy, diethylaminocarbonyloxy, benzylaminocarbonyl, acryloyl, propioloyl, cyclopentyl, cyclohexyl, dou- bly attached propanediyl or ethyleneoxy, each of which is optionally mono- to tetrasubstituted by identical or different substituents from the group consisting of fluorine, chlorine, oxo, methyl, and trifluoromethyl, and a grouping

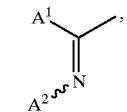

where $A^1$ represents hydrogen, methyl or hydroxyl and $A^2$ represents hydroxyl, methoxy, ethoxy, amino, methylamino, phenyl or benzyl; or phenyl, phenoxy, phenylthio, benzoyl, benzoylethenyl, cinnamoyl, benzyl, phenylethyl, phenylpropyl, benzyloxy, benzylthio, 5,6-dihydro-1,4,2-dioxazin-3-ylmethyl, triazolylmethyl, benzoxazol-2-ylmethyl, 1,3-dioxan-2-yl, benzimidazol-2-yl, dioxol-2-yl, or oxadiazolyl, each of which is optionally mono- to trisubstituted in the ring moiety by halogen and/or straight-chain or branched alkyl or alkoxy having 1 to 4 carbon atoms, X represents fluorine, $L^1$, $L^2$, $L^3$, and $L^4$ each represent hydrogen, and $L^5$ represents one of the groups:

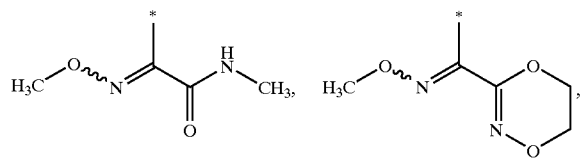

where * denotes the point of attachment to the phenyl radical of formula (I).

* * * * *